US010772371B1

(12) United States Patent
Sabin

(10) Patent No.: US 10,772,371 B1
(45) Date of Patent: Sep. 15, 2020

(54) ALL WEATHER ELECTRIC INDOOR/OUTDOOR HEAT EXCHANGER FACE MASK

(71) Applicant: Robert Sabin, Mill Neck, NY (US)

(72) Inventor: Robert Sabin, Mill Neck, NY (US)

(*) Notice: Subject to any disclaimer, the term of this patent is extended or adjusted under 35 U.S.C. 154(b) by 0 days.

(21) Appl. No.: 16/798,143

(22) Filed: Feb. 21, 2020

(51) Int. Cl.
*A42B 1/00* (2006.01)
*A41D 13/11* (2006.01)
*A42B 1/24* (2006.01)
*A41D 13/005* (2006.01)

(52) U.S. Cl.
CPC .......... *A42B 1/008* (2013.01); *A41D 13/0051* (2013.01); *A41D 13/1161* (2013.01); *A42B 1/24* (2013.01); *A41D 13/11* (2013.01); *A41D 2400/10* (2013.01)

(58) Field of Classification Search
CPC ............... A41D 13/0051; A41D 13/11; A41D 13/1161; A41D 13/1192; A41D 2400/10; A41D 2400/12; A42B 1/008; A42B 1/24; A62B 9/003; A61M 16/1065; A61M 16/107; A61M 16/1075; A61M 16/108; A61M 16/1085; A61M 16/106
See application file for complete search history.

(56) References Cited

U.S. PATENT DOCUMENTS

| | | | | |
|---|---|---|---|---|
| 2,626,343 A | * | 1/1953 | Fogel ..................... | H05B 3/342 219/211 |
| 2,784,714 A | * | 3/1957 | Pitzipio .................. | A62B 9/003 128/204.17 |
| 3,249,108 A | * | 5/1966 | Terman ................... | A61F 7/007 128/204.17 |
| 4,458,679 A | * | 7/1984 | Ward ..................... | A61M 16/06 128/201.13 |
| 4,573,464 A | * | 3/1986 | Yo ......................... | A62B 18/10 128/206.15 |
| 4,601,287 A | * | 7/1986 | Royce, Jr. .............. | A62B 23/02 128/204.17 |
| 4,620,537 A | * | 11/1986 | Brown ................. | A62B 18/025 128/201.13 |
| 4,793,343 A | * | 12/1988 | Cummins, Jr. ... | A61M 16/1075 128/203.27 |
| 4,905,686 A | * | 3/1990 | Adams ................. | A61M 16/06 128/204.17 |

(Continued)

*Primary Examiner* — Amy Vanatta
(74) *Attorney, Agent, or Firm* — Alfred M. Walker; John F. Vodopia; Jennifer Yancy

(57) ABSTRACT

A face mask apparatus is formed with a breathing chamber that provides adjustable warm and humidified air for inhalation. The breathing chamber heats cold air that is breathed in through the face mask during normal breathing, which is worn over the nose and mouth of a person. A temperature gauge monitors temperature for future adjustment of the amount of heat generating current. The air in the chamber is heated for inhalation by a resistive carbon fiber tape. The temperature of the resistive material (and by extension the warm air generated), is regulated/adjusted by increasing or decreasing the current output settings on the power source. Warm and humidified air is produced. The face mask may be part of a balaclava hood or a hat, or to other head gear, or as a stand alone with straps around the head, optionally with an adjustable solar powered battery.

33 Claims, 10 Drawing Sheets

(56) References Cited

U.S. PATENT DOCUMENTS

| | | | | | |
|---|---|---|---|---|---|
| 5,435,299 | A | * | 7/1995 | Langman | A62B 9/003 |
| | | | | | 128/201.13 |
| 5,511,541 | A | * | 4/1996 | Dearstine | A62B 9/003 |
| | | | | | 128/201.13 |
| 5,570,684 | A | * | 11/1996 | Behr | A61M 16/06 |
| | | | | | 128/201.13 |
| 5,884,336 | A | * | 3/1999 | Stout | A62B 9/003 |
| | | | | | 128/205.27 |
| 2011/0297152 | A1 | * | 12/2011 | Duveen | A61M 16/06 |
| | | | | | 128/203.29 |
| 2015/0173445 | A1 | * | 6/2015 | Gordon | F25B 21/04 |
| | | | | | 62/3.3 |
| 2015/0230524 | A1 | * | 8/2015 | Stevens | H05B 3/34 |
| | | | | | 219/211 |
| 2019/0069611 | A1 | * | 3/2019 | Potnis | A41D 13/0056 |
| 2019/0321661 | A1 | * | 10/2019 | Vanderham | A61M 16/0605 |

* cited by examiner

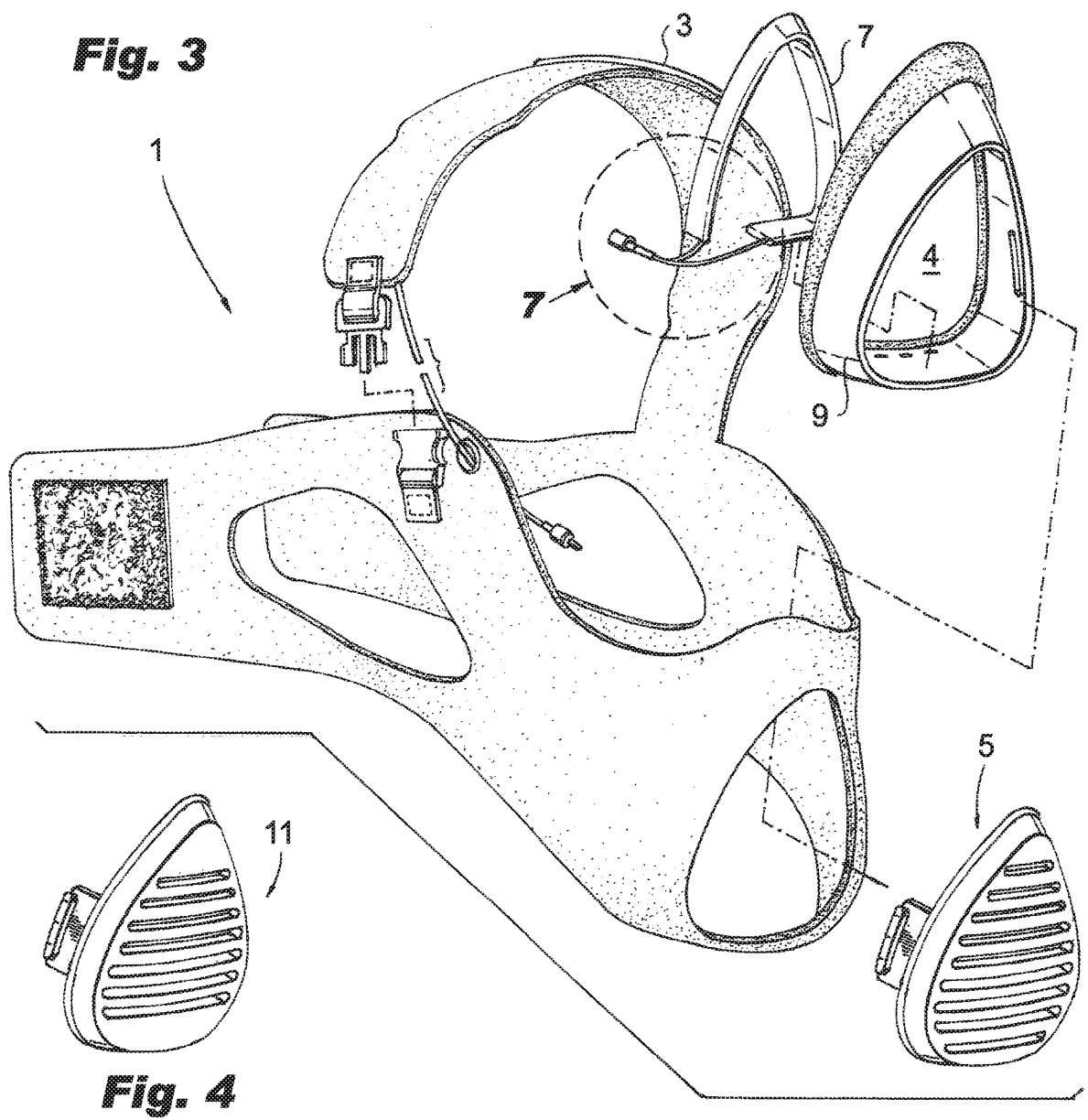
Fig. 3
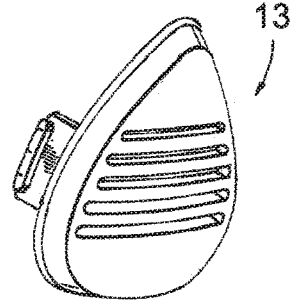
Fig. 5
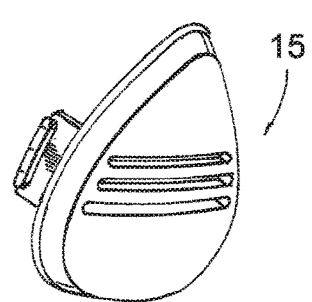
Fig. 6
Fig. 4

ALL WEATHER ELECTRIC INDOOR/OUTDOOR HEAT EXCHANGER FACE MASK

FIELD OF THE INVENTION

This invention relates to a face mask and method for using the face mask in all-weather indoor and outdoor conditions, 24 hrs. a day/7 day a week, to condition air drawn into the face mask before it is actually breathed and thereby supply warm and humidified air to persons in need thereof, particularly in extremely cold weather, e.g., in freezing and/or below freezing weather.

BACKGROUND OF THE INVENTION

All references are included in their entirety as if reproduced in full herein.

It is well established that cold weather, and particularly cold air, can play havoc with your lungs and health. See American Lung Association, "COLD WEATHER AND YOUR LUNGS". See, "Why Breathing Cold Air Hurts When You're Running", Runners World, William O. Roberts MD Dec. 3, 2019, More than 60 million people run or Jog in the United States, and more than 110 million people participate in walking for fitness. Cold air is often dry air, which dry air is often a killer, causing much mortality and morbidity, especially for those with lung diseases. See COPD among adults in NY disclosing that 15 million Americans have been diagnosed with (COPD), Airway diseases (see NIH, NIEHS, "Lung Diseases", revised 2020,) also can cause discomfort, mortality and morbidity.

The Center for Disease Control and Prevention (CDC) discloses that "Chronic lower respiratory diseases" are the 4th. leading cause of death in the United States in 2018. Dry cold air can irritate the airways of people with asthma, CDC discloses in excess of 25 million Americans have Asthma. See NIH, NIEHS, "Lung Diseases", revised 2020, Moreover, there are many patients with Lung Cancer, heart disease, and other diseases and irritations of the lung and airways, any respiratory condition, who are in need of a safe, temperature adjustable, cost-effective, portable, non-burdensome intervention to warm cold inhaled air and all other air, to humidify said air. Sleep Apnea Statistics show that the current population of the United States is 326 million, 10% of which have mild obstructive sleep apnea. This translates to 32.6 million people who could possibly benefit from applicant's invention. Moreover, there are an estimated 22 million Americans who suffer from moderate to severe sleep apnea, many of these could benefit from applicant's invention. People with cardiac conditions also could benefit from applicant's invention. See "The Sleep Zone, "Sleep Apnea Statistics" Feb. 9, 2018. See also US EPA, "Asthma continues to be a serious public health problem in the United States", EPA-402F-04-019, May 2018.

Air Guard discloses some, but not all, of the people who could benefit from the inhalation of warm, humidified air. The medical costs caused by cold dry air is in the many billions. The suffering is incalculable. See The-perfect-present.com, "Air Guard Medical CT Cold Air Winter Face Mask". website, 2019.

The simplest way to heat inhaled air is a scarf wrapped around the mouth and nose. This has been used for hundreds of years. It works to some degree. It is awkward, restricts breathing, impairs speaking, cumbersome, accumulates moisture and germs, and is stifling and claustrophobic, the more it is wrapped around the face, the more restrictive the breathing becomes.

Cold Weather masks have been developed to fill this huge unmet medical, athletic, and other need. Laura Johannes in the Wall Street Journal, reports, "A Breath of Warm Air on a Cold Day", testing of Four cold weather masks in Boston in 25-degree weather. The tests involved cross-country skiing, and biking. She tested the two main technologies currently used, namely a heat exchanger, with a copper mesh installed directly in front of the mouth. Polar Wrap. This works by the exhaled air heating the copper mesh, and the inhaled air trafficking over the heated copper mesh, heating and humidifying the cold air before it is inspired to the lungs. The second one used, Psolar inc., used a heat absorbing plastic directly in front of the mouth, with a desiccant to absorb moisture.

The third model used and discussed by Johannes, supra, ColdAvenger™ has a chamber in front of the mouth without a heat exchanger, so that the cold inspired air mixes with the warm expired air in the chamber, is heated, humidified, and inspired into the Lung. The CT mask was also tested; it is a copper mesh heat exchanger in front of the mouth. It has a severe restriction of breathing, i.e., it obstructs air flow and requires a large amount of work from a user's diaphragm to get the air in.

This article of Johannes, W S J op cit above] discloses the main failings of both approaches. The HME (heat moisture exchanger) masks restrict breathing with the heat exchanger copper or other heat sink material or mesh directly in front of the mouth, or in the airflow leading to the mouth, no exceptions. Anything between the mouth and the airflow impedes inhalation and exhalation causes restriction and impedes breathing. The HME masks are claustrophobic, impair speaking, are not heated air And Humidity adjustable, and they accumulate moisture and germs.

The ColdAvenger™, with an empty chamber in front of the mouth, without a heat exchanger, in front of the mouth, has superb breathing without air restriction. Moreover, the ColdAvenger produces little heated air if anything, as noted in Applicant's extensive personal experience. "Heat exchanger masks—a Love Story" (www.coldbike.com/2019/02/13/heat-exchanger-masks-a-love-story/), also discloses, in reference to the ColdAvenger, "No real heat exchange only a pocketful of exhaled breath at the mouth". Heat exchanger masks—a Love Story also discloses in reference to the Polar wrap heat exchanger, "Like breathing through a straw" AND "This is the best device for waiting for the bus" Thus in the art the empty chamber model produces little or no heated air or humidity, the Heat moisture Exchanger produce some heated air and increased humidity, with severe restriction/inhibition on breathing.

See "THE CARDIOPULMONARY EFFECT OF A HEAT AND MOISTURE EXCHANGE MASK ON COPD PATIENTS DURING COLD EXPOSURE" John G. Seifert, PhD June 2009—which discloses a mask that works in the COPD patient during cold exposure. Siefert discusses "Recovery benefits of using a heat and moisture exchange mask during sprint exercise in cold temperatures" which discloses HME (Heat and moisture exchange masks) mask works compared to no mask.

See NIH, NIEHS, "Lung Diseases", which describes lung diseases.

See also "Efficacy of a heat exchanger mask in cold exercise-induced asthma" of Beuther D A, Chest 2006 May; 129(5):1188-93, which describes a mask that works as well as the drug albuterol pretreatment.

See also Rodrigo Athanazio, "Review—Airway disease: similarities and differences between asthma, COPD, and Bronchiectasis", Clinics 2012; 67(11): 1335-1343, 2012, which discloses the diseases, risk factors, pathophysiology, symptoms, diagnosis, and treatment of diseases amenable to use with applicant's invention.

See also Maria D'Amato at al, "The impact of cold on the respiratory tract and its consequences to respiratory health", et al. Clinical translation Allergy, (2018) 8.20, which discloses the negative effects of cold air in indoor environments such as cars, offices, homes, shopping centers, hotels, nursing homes, hospitals, and the like.

The aforementioned references describe circumstances which can be characterized as perfect places for the applicant's invention. Another huge advantage of the invention is that in the same room of any facility, each individual's inspired warm air can be custom tailored, (bespoke), to that specific individual. In fact, each individual outside or inside can have a custom tailored bespoke warm air inhalation profile.

U.S. Pat. No. 4,793,343 of Cummins, for a respiratory heated face mask, which discloses a face mask with an electric heater element. This is different than the applicant's invention in that it has an extended air inlet (24), nothing in or on the housing (18), and a severely restrictive heater element directly in front of the mouth, (54), a restrictive filter (48), and a further restrictive threaded cap, and further restrictive air inlets and air outlets with check valves, (26,34,32,36,38,40).

U.S. Pat. No. 5,551,584 of Dearstine discloses an electrically powered face mask. A severe fatal shortcoming of this reference is that as shown on Cover Page and FIG. 1 There are two air inlet ports, 28 and 32, on both sides of the face, with inlet port 30, directly above the mouth. Every animal from the ant to the elephant has the mouth and air intake directly in front, or slightly behind the nose, through the mouth. It doesn't work any other way. It would be an extreme restriction, extreme difficulty, or extreme unworkable burden on air inhalation to try to inspire air from both sides of the face, and the front port, and therefore Dearstine '584 is substantially unworkable. Furthermore, to open these three inlet ports requires much energy, which is additional restriction of inhalation. Dearstine '584 at column 1, reference claims twice, "Warm and dry the face of a wearer" Dearstine '584 at column 2, line 65, says the same thing. This reference of Dearstine '584 discloses or claims nothing about heating or humidification of the air for inhalation of the "face of a wearer": See Dearstine '584 at column 1, Field of the invention, and at column 1, second to last paragraph. Applicants other aforementioned prior references disclose that dry air is very harmful for inhalation, although the Dearstine '584 reference does not disclose warming or humidification of air for inhalation, nor humidification of the air for inhalation. The Dearstine '584 reference exclusively discloses warming the face.

The Dearstine '584 reference also claims at column 2, lines 45-48, a cost-effective invention for manufacture and marketing. Applicant differs with 4 separate distinct inhale and exhale flaps; see Dearstine '584 at column 4, lines 19-21, taken together with the requirement of two batteries, see Dearstine '584 at FIG. 7; therefore, this Dearstine '584 reference is not cost-effective to manufacture. This reference claims an array of electrical resistance wires for generating heat, positioned in each inhale port with wire attachments to these electrical resistance wires, provides additional resistance to the airflow inhalation of air.

Moreover, as disclosed in the invention, after the person exhales the exhalation flap closes, so that the mask is empty, and then air warmed by the electrical wires heats the oncoming air and warms the face. This reference discloses or claims nothing about heating or humidifying air for inhalation.

Additionally, a common prior art non-heated N95 face mask (i.e., Moldex 2200 N95 Particulate Disposable Respirator) overlays and encircles the nose and mouth of a person when installed with the straps extended behind the head. They are commonly available at Home Depot and the like, used for decades, in the millions, to block paint, sawdust, pollen, dust, sand, dirt, and other small particulates.

Applicant travels to Canada every year for the last 16 yrs. to photograph polar bears in minus 50 Degree temperature to minus 20-degree temperature for weeks at a time. Applicant has used the Polar Wrap Heat exchanger mask, (copper mesh) extensively during this time. While it does heat the inspired cold air, it also displays the problems noted above associated with the prior art devices. While using the polar wrap heat exchanger mask does modify what could be minus 40-50-degree cold air, there is much room for improvement. Applicant certainly can use increased air temperature, without claustrophobia, and restriction, etc.

Applicant also tent camps in Alaska, with a small lightweight solar Cell Light, which works very well, the solar battery of this light, with its adjustable current output and small size, is ideally suited for use in the applicant's invention. Moreover, the applicant in New York has extensively and successfully used a 7.4V battery heated gloves, which work great, and the 7.4V battery or less, 5V, or 3.7V batteries are ideally suited for use in the applicant's invention, or non-rechargeable/disposable batteries.

Applicant has also used the ColdAvenger™ chamber cold weather mask. It supplies little or no heat, as noted by the Wall Street Journal article of Laura Johannes, but it has little or no restriction on breathing.

OBJECTS OF THE INVENTION

The inventive face mask and method overcome the shortcomings of the prior art as explained above.

The objects, features, and advantages of this invention are to help people and to provide an apparatus to help people disclosed in the Background of the invention above, in what is thought to be a safe cost-effective manner.

It is an object of the invention that the face mask breathing apparatus be affixed to the head with straps with Velcro®, buttons, plastic snap connectors, (see drawing FIG. 1) buckles and the like.

It is also an object of the invention that it be portable, stand alone, or to be worn over Balaclava-type headgear, with hats, with scarves etc. People are very sensitive to fit, so that it is better that they wear the invention over their current balaclava headgear.

It is also an object of the invention that it can used as a stand-alone apparatus without any hat, say in nursing homes or hospitals or supermarkets etc. It is preferred that the balaclava be cut away around the mouth and nose to minimize small restriction of air, not necessary but preferred.

It is further an object of the present invention to provide an ergonomic heated face mask with a relatively shallow nasal/mouth breathing chamber, without awkward and unwieldly protuberance nasal/mouth breathing chambers.

Other objects of the invention will become apparent from the following description of the present invention.

SUMMARY OF THE INVENTION

In keeping with these objects and others which may become apparent, the present invention is a face mask apparatus (or "face mask") which is bespoke with structure that conditions incoming (typically cold or very cold) air, e.g., warms and humidifies air for inhalation, in outdoor and indoor conditions, sleeping or awake, resting or ambulatory. This face mask apparatus is adaptable for use by all people in need, including but not limited to, persons with medical conditions relating to the lung and airways, such as asthma and COPD, heart disease, with athletic conditions such as cycling, skiing, running, emergency responders to accidents including hypothermia, etc.

The inventive facemask is useful for outdoor workers, members of the military, outdoor workers and the like, for example, anyone, of any gender, virtually any age, who would benefit from bespoke warm and humidified air inhalation, hypertension, for example. In applicant's face mask, cold air is heated and continuously supplied through in response to the normal breathing process through the face mask apparatus, which is worn over the nose and mouth of a person. A temperature gauge is installed on the exterior surface of the chamber with the probe inserted within the chamber, for monitoring temperature for future adjustment.

Any air, cold, warm, or cool, is heated for inhalation by a resistive material affixed inside the breathing chamber, which when a current is applied, generates heat. The resistive material may be embedded/encapsulated or attached to the surface of the chamber, and covered in the chamber, analogous to the radiant heating of floors, or the entire chamber may be made out of resistive material. The temperature of the resistive material (and by extension the warm air generated), is regulated/adjusted by increasing or decreasing the current output settings on the power source, for example a 3.7 V lithium ion battery or a 7.4V Lithium ion battery, which is connected and wired to the carbon fiber resistive material inside the breathing chamber, which has on/off and 4 output settings. 25%, 50%, 75% and 100% of current output, indicated by red LEDs, or, an action heat lithium ion battery, with three (3) heat settings, warm and humidified air is produced having an adjustable temperature range of about 40 Degrees F. to 95 Degrees F+. The resistive material is powered by a lithium ion battery, as above, and/or, an attached to the face mask apparatus, which may be part of a balaclava hood or a hat, or to other places, optionally with an adjustable solar powered battery. The heat mask can preferably have a current limiting device that can limit the amount of current that can surge in the power circuit.

In an embodiment, the invention supplies humidified adjustable warm air, without restriction to breathing, unlike the ColdAvenger™. The inventive face mask and method of use enables unrestricted breathing with humidified heated air, unlike the Polar Wrap, CT, or Polar mask Preferably, the amount of heat and humidity to be actually inhaled (post conditioning in the breathing chamber is sensed, and is adjustable according to the inventive principles. The heated face mask of the present invention is provided with an ergonomic, relatively shallow nasal/mouth breathing chamber, without awkward and unwieldly protuberance nasal/mouth breathing chambers of the prior art.

Bespoke, in fact, applicant believes his invention can increase athletic performance in most all weather, all temperature climates, by adjusting to the optimum temperature and humidity to be breathed in for peak performance that specific day, bespoke, those specific conditions, of temperature and humidity, and physical characteristics of the person, instead of being stuck and inhaling, whatever you get if anything with all the others. The invention enables that in the same room of any facility, each individual's inspired warm air can be custom tailored, (bespoke) to that specific individual so each individual outside or inside can have a custom tailored bespoke warm air inhalation profile, that is reproduced according to the face mask settings.

The face mask for conditioning air to be breathed, includes:

a facial covering having an inner surface and an outer surface and configured to be removably positioned over a user's mouth and nose, thereby forming a breathing chamber with an inner volume in which air to be breathed is conditioned;

wherein the breathing chamber includes an opening through which the air to be breathed is drawn and air to be exhaled is expelled;

an inner frame with an inner and outer surface, wherein the outer surface of the inner frame is attached to the inner surface of the facial covering about the opening; and conditioning means arranged in the breathing chamber on the inner surface of the inner frame to condition air drawn into the breathing chamber. The inner frame is preferably concave shaped.

The electric heating element is preferably resistive carbon fiber tape. Preferably, the conditioning means includes a source of electrical power for the electric heating element.

The air to be breathed and/or to be exhaled traverses a path through the inner volume between a user's mouth and/or nose, and the opening in the breathing chamber, surrounded by the inner surface of the inner frame.

The opening in the breathing chamber is formed to receive a detachable inlet plate or valve, wherein the air to be breathed is drawn through the inlet plate or valve and air to be exhaled is expelled through the inlet plate or valve, and the inlet plate or valve is formed with openings for air passage.

Preferably, the inlet plate or valve is detachably connected to the inner frame fixed to the inner surface of the breathing chamber, such as, for example, by using a snap or bayonet mount.

The inlet plate or valve is formed with openings in the form of slit patterns, wherein each of the slit patterns is configured to define different resistance to breathing air through the inlet plate or valve. The different resistances associated with the different slit patterns supports air resistance training by athletes using the face mask.

Optionally, the breathing chamber is formed with weep holes through which moisture generated as condensation when cold air mixes with moist, warm exhalation air can drain, and optionally, the weep holes are arranged in a bottom of the breathing chamber.

Optionally, the inner frame also includes weep holes that align with the weep holes within the breathing chamber.

The facial covering and inner frame are optionally manufactured from a material selected from the group of materials consisting of medical grade polyurethane, medical grade neoprene, medical grade silicone, and like materials.

The source of electrical power is preferably a battery attached to the facial covering and electrically connected to the conditioning means, wherein preferably the battery is rechargeable.

Optionally, there is included a solar-based charging system for recharging the battery and/or a filter unit that filters are to be conditioned prior to breathing. Preferably, the charging system is an alternating power generating system, for powering the face mask.

The present invention also optionally comprises a method of conditioning air to be breathed in reliance upon a face mask that comprises a facial covering having an inner surface and an outer surface and which is configured to be removably positioned over a user's mouth and nose, thereby forming an breathing chamber with an inner volume in which air to be breathed is conditioned, an inner frame with an inner and outer surface, attached to the inner surface of the facial covering within the inner volume about the opening and conditioning means arranged in the breathing chamber on the inner surface of the inner frame to condition air drawn into the breathing chamber.

The method optionally further comprises the steps of:
a) attaching the facial covering to a user's face so that it covers the user's mouth and nose to form the breathing chamber and inner volume;
b) activating the air conditioning means;
c) breathing air outside the face mask into the inner chamber, to mix (and preferably heat and humidify) the outside air with exhaust air in the inner volume, and;
d) realizing a mixture of air drawn into the user's air passages that is warmer and moister than the outside air.

The method also comprises the face mask including an on/off button (preferably on the battery), and wherein upon activating the button to an on state, a predetermined current is provided to the resistive carbon fiber tape in the breathing chamber.

The method also includes preferably wherein the face mask has a temperature sensor and wherein the temperature sensor senses a temperature outside the face mask and adjusts an amount of electrical power to be supplied to the resistive carbon fiber tape based thereon.

Preferably, the resistive carbon fiber tape is attached to the inner surface of the inner frame in a pattern selected from a group of patterns consisting of horseshoe, crescent or otherwise curved u-shaped patterns.

Optionally, the resistive carbon fiber tape is affixed to the inner surface of the inner frame using any of silicone rubber, rubber cement, epoxy and other adhesive agents.

The method also includes the predetermined current, which is optionally is defined by a battery, such as, for example, a lithium ion 7.4V battery, a lithium ion 5V battery, a lithium ion 3.7 V battery, or any battery with sufficient current to warm and generate heat from the resistive carbon fiber material.

The amount of current supplied is preferably adjustable manually. The current is adjusted manually by pressing buttons on the face mask, for example, on the lithium ion battery to increase or decrease current, or remotely by a controlling device such as a specially programmed key-FOB-like device.

Optionally, the heated face mask can be used in conjunction with eye protective goggles.

BRIEF DESCRIPTION OF THE DRAWINGS

The present invention can best be understood in connection with the accompanying drawings. It is noted that the invention is not limited to the precise embodiments shown in the following drawings, in which:

FIG. 3 is a partial exploded view of the face mask of this invention with a full inlet plate.
FIG. 4 is a perspective view of a three quarters inlet plate.
FIG. 5 is a perspective view of a half inlet plate.
FIG. 6 is a perspective view of quarter inlet plate.

DETAILED DESCRIPTION OF THE INVENTION

Figure 1:
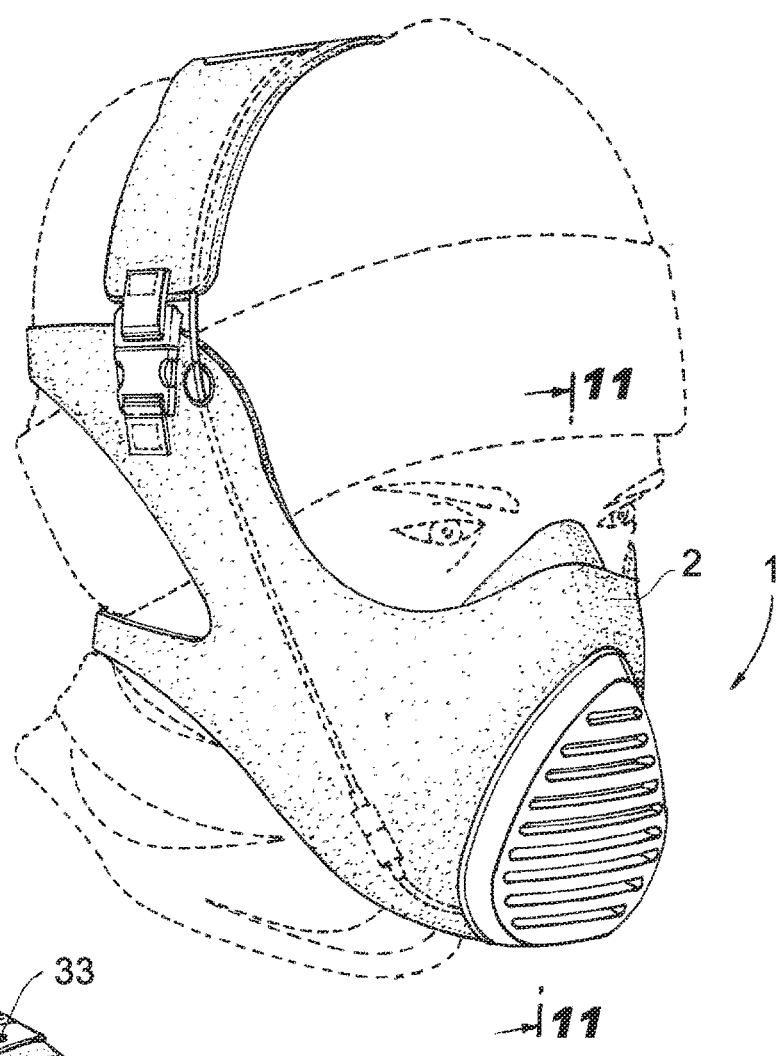
FIG. 1 is a front perspective view of a user wearing a heat exchanger (HE) face mask of this invention.

Applicant's face mask apparatus (or "face mask") 1, which is constructed according to the inventive principles, presents with a similar view in profile to the aforementioned N95 face mask, known in the prior art. See FIGS. 1-3 for a breathing chamber that is shaped by an inner frame 9 (which is preferably concave) having both an interior and exterior surface. An outer surface of the inner frame 9 is attached to an inner surface of the facial covering 2. The physical dimensions of the inner frame 9 define the physical dimensions of the breathing chamber. A resistive carbon fiber tape 7 is installed in the inner frame within the breathing chamber. Preferably, there are weep holes 21 on the bottom of the inner frame 9 and/or the facial covering to drain moisture, i.e., condensation precipitated when cold air taken into the breathing chamber from the outside meets the warm, moisture-laden air exhaled by the user into the inner air volume 4 of the breathing chamber. The weep hole(s) control(s) moisture content of the air to be breathed. The inner frame 9, or breathing chamber structural housing, is preferably manufactured out of medical grade polyurethane, medical grade neoprene, medical grade silicone, or other medical grade polymers. The preferred material is medical grade polyurethane or medical grade neoprene. The material comprising the inner frame 9 may be the same material as the facial covering or a combination of the disclosed materials. The material comprising the facial covering 2 may be any material, such as natural and man-made cloths, leather, processed paper, etc., as known to one of ordinary skill in the art, for making medical and non-medical face masks. The heated face mask includes a relatively shallow nasal/mouth breathing chamber, without awkward and unwieldly protuberance nasal/mouth breathing chambers.

A preferred method of use of the inventive face mask is with a scarf or Balaclava, so that the face mask apparatus beds down nicely on the Balaclava or scarf material. For that matter, a proximal edge of the walls of the breathing chamber (i.e., formed by inner frame 9), and/or the facial covering, except to the portion with the hole or opening 4, rests in a flush with the user's face. Preferably, the edge is quasi airtight. The Balaclava or scarf material is preferred to affix a battery or solar battery, that is electrically connected to an electric element (for example, resistive carbon fiber tape), as will be explained in greater detail below.

It is notable that the weight of the inner frame 9 installed in the mask 1 is preferably less than one (1) ounce due to the light weight nature of the resistive carbon fiber tape 7 that is relied upon for heating and otherwise conditioning the air to be breathed. Preferably, the aggregate weight of the battery 25 and carbon fiber tape 7 is less than 4 ounces. An optional larger battery 27 for the face mask apparatus 1 may be placed in a shirt pocket, purse, scarf, neck warmer, balaclava and the like. The face mask apparatus 1, plus the electrically resistive carbon fiber tape members 7, within the face mask 1 is very light weight. It is remarkable how the face mask 1, being so small, unobtrusive, and lightweight, can do so much. In fact, there is no way of visually seeing the electrically resistive carbon fiber tape 7, or tapes, is/are installed in the face mask 1 from the outside (preferably in the inner frame 9), except for the thin wires leading away from the resistive carbon fiber tape, out of the mask. The battery may be installed on the mask itself, or in a garment proximate the mask.

As shown in FIG. 3, on the front of the face mask apparatus 1 is an inlet plate or valve 5 that connects to the inner frame and covers breathing hole or opening 4 of the inner frame 9. The inlet plate or valve 5 is formed with vertical slots, or horizontal slots, or both, that is turned to define air intake resistance for air intake and air exhalation. This inlet plate or valve 5 affixes to the breathing chamber 9 or housing with a snap or bayonet mount, to affix to the inner frame 9 or housing, or reverse twist to remove. The inlet plate or valve 5 is interchangeable with other inlet plates/valves 11 (see FIG. 4), 13 (see FIG. 5) or 15 (see FIG. 6) with different slits for different levels of air intake and exhalation, i.e. for air resistance training of athletes.

The face mask 1 of the present invention can be used for both heated air and humidity, and by switching inlet plate or valve 5, 11, 13 or 15, for air resistance training, all rolled up into one unit. There may be an additional inlet plate, valve or filter plate (not shown) with a filter for particulates as an option, or a combination of an inlet plate or valve with slit and a filter. The entire inlet plate or valve 5, 11, 13 or 15 may be removed for competitive athletic events.

Without being limited, held, or bound to any particular theory or mechanism of action of the invention, it is thought that the electric current supplied to the carbon fiber tape or tapes 7 heats the lightweight tape, which heats the air within the breathing chamber formed by inner frame 9. When a person inhales the cold or cool air is heated and humidified in the breathing chamber by the turbulence of the mixing of hot and cold air, then the warm and humidified air is inhaled fully to the lungs. The nose and passages there are also warmed and humidified.

Figure 8:
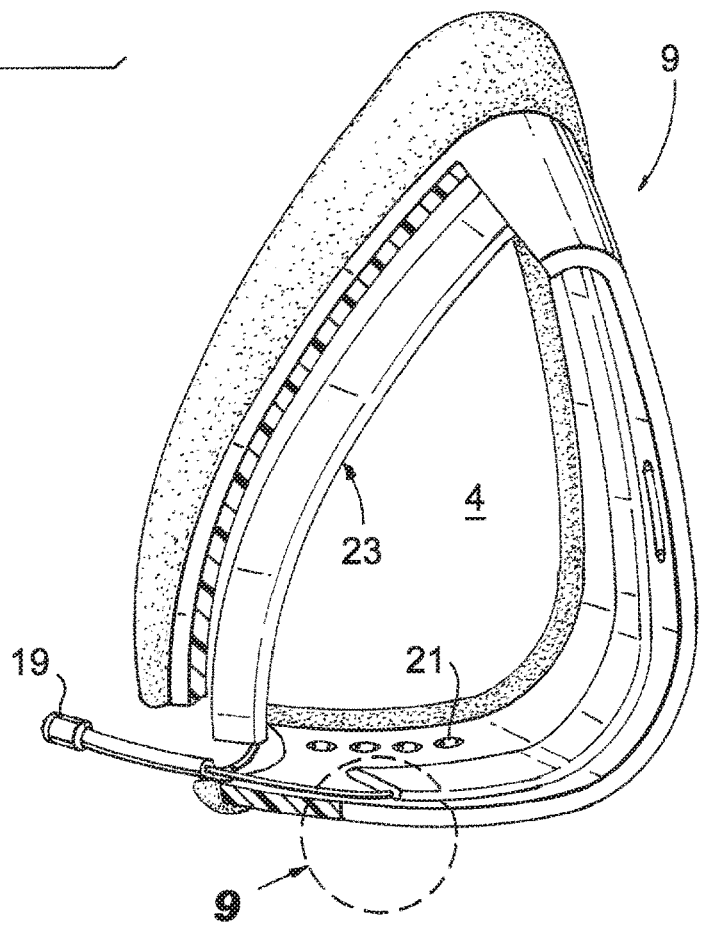
FIG. 8 is a perspective view of heat chamber section with a horseshoe shaped heat tape element.
Figure 10:
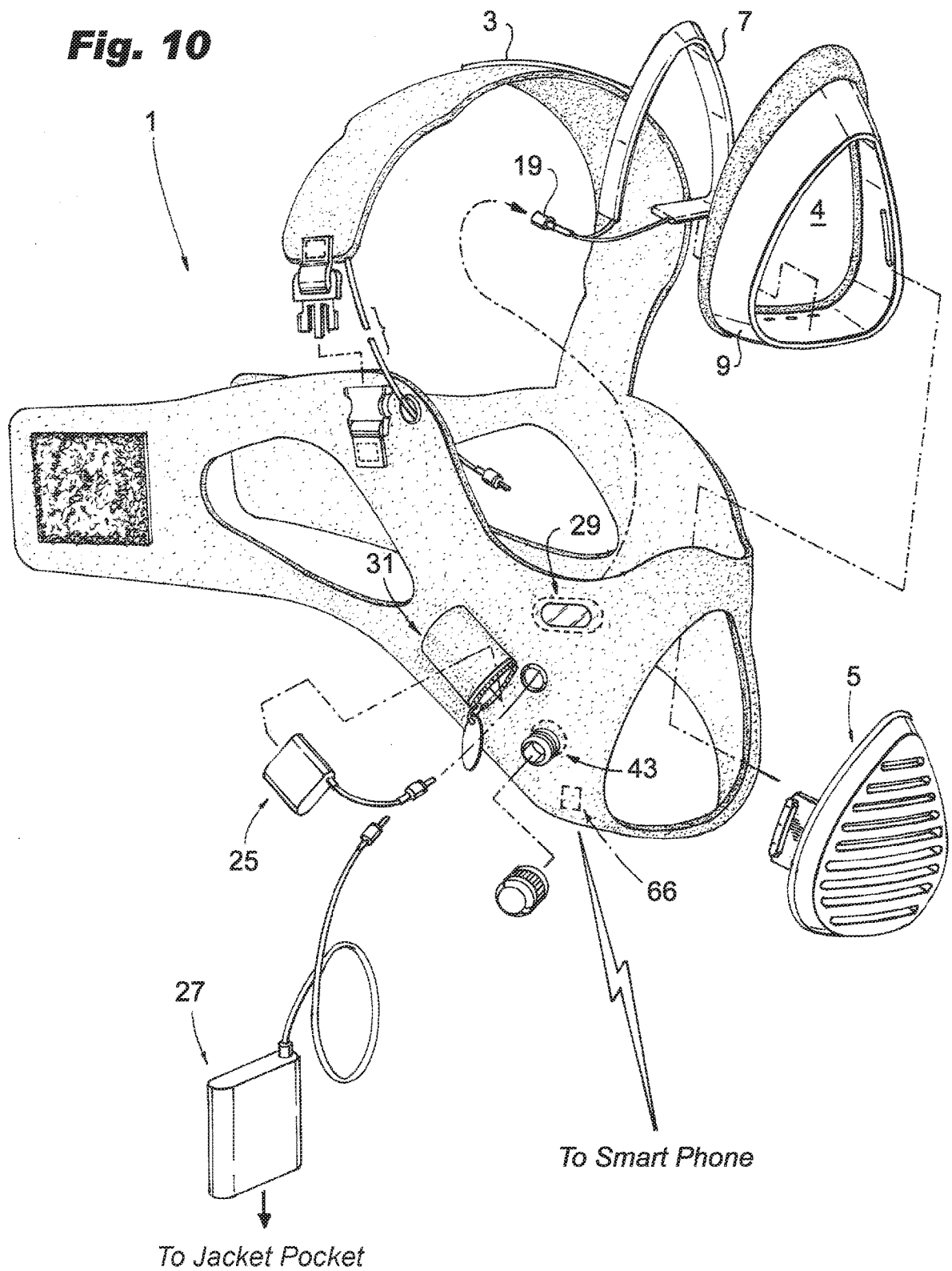
FIG. 10 is a perspective/exploded view of the HE face mask of this invention showing more details of components and placement.
Figure 11:
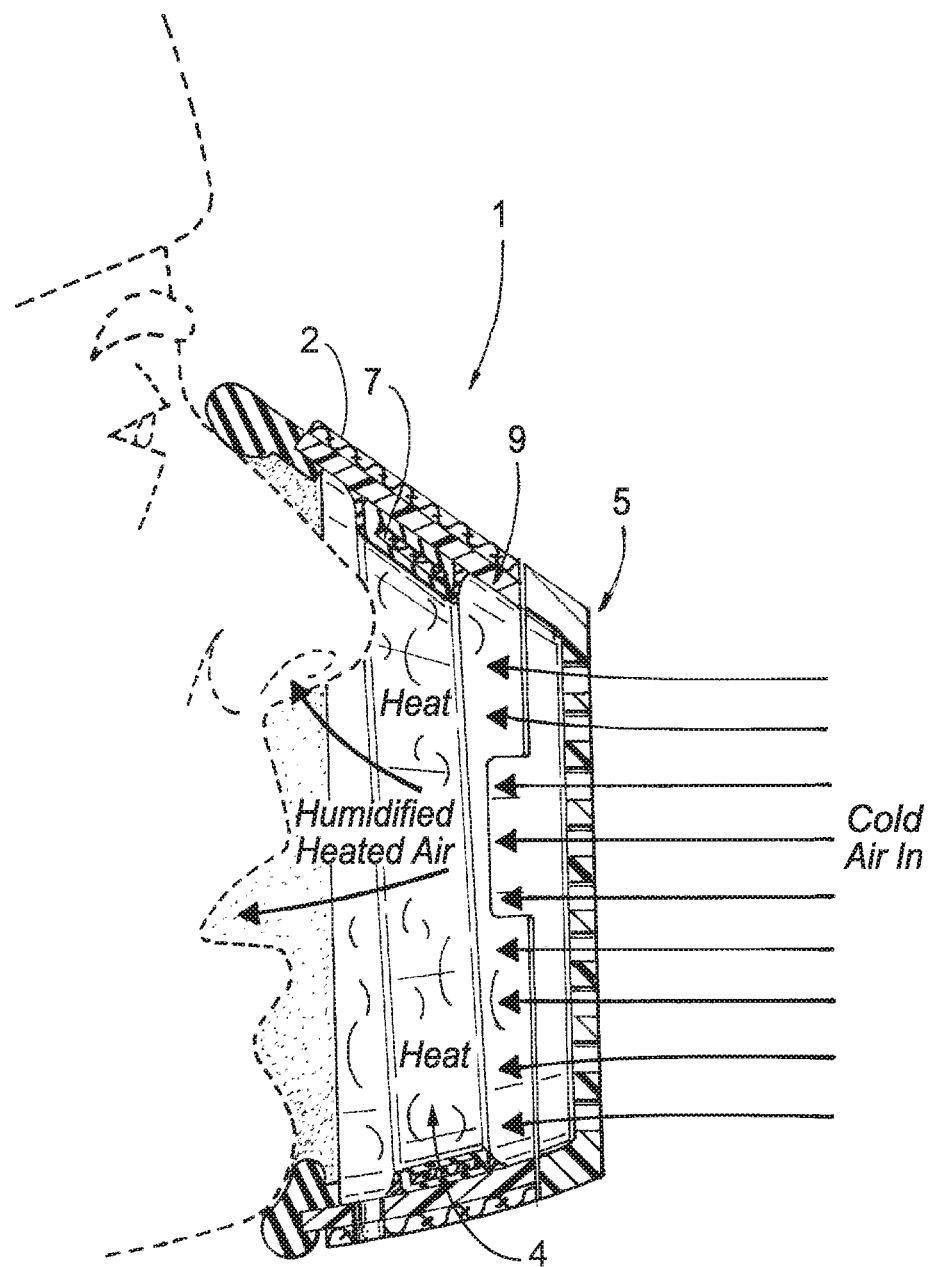
FIG. 11 is a side view cross section of the heat chamber.

The interior of the applicant's face mask is shown in exploded views of FIGS. 8, 10 and 11, looking down at the inner frame 9 (and breathing chamber) from inside the face mask 1.

Figure 7:
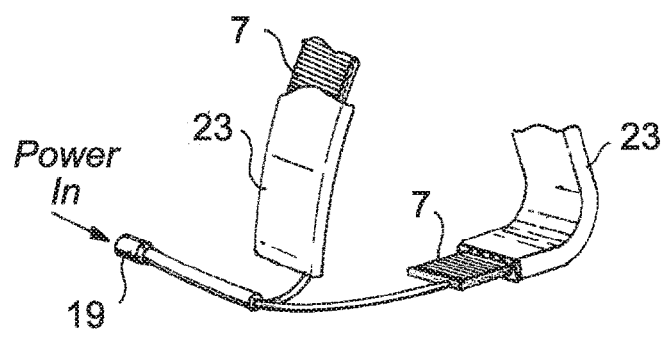
FIG. 7 is an enlarged detail of the tape/weave/cable connection.

The electrically resistive carbon fiber tape 7 used is a resistive material which, when a current is applied, generates heat FIG. 10 shows the installation of the resistive carbon fiber tape 7 in a crescent horseshoe manner. The horseshoe shape for the electrically resistive carbon fiber tape 7 is the preferred shape within the breathing chamber. The carbon fiber tape 7 is affixed to the interior (e.g., inner surface) of the inner frame 9 with silicone rubber, rubber cement, epoxy or other adhesive agents. As shown in the close-up detail view of FIG. 9, a light brush coat of silicone rubber or other sealant is applied over the carbon fiber tape member 7. As shown in FIG. 7, two separate wires affixed to the carbon fiber tape 7 on opposite sides of the tape 7, extend from within the breathing chamber 9 (defined by the contour of inner frame 9 when its proximal edges contact the person's face/head) to outside the inner frame 9, to the lithium ion 7.4V battery, lithium ion 5V battery, lithium ion 3.7V battery, or any known battery 25 with sufficient current to warm the resistive carbon fiber material of carbon fiber tape member 7, or to a solar cell 59 with an attached battery, as shown in the electrical schematic diagram FIG. 17.

The preferred resistive material is an electrically resistive carbon fiber tape 7, viscose based, also used as a biocompatible material used for wound healing and human body implants. It feels like fine silk. It is safe. As importantly, it is substantially fight weight to minimize the obtrusiveness of wearing a face mask. There is a long-established history with this resistive carbon fiber tape 7 for electric heated clothing, including knee wrap, gloves, sleeping bag, heated gloves, heated beanie, heated insoles, heated modular vest, etc. See the prior art documents of "You can do it", see DIY carbon heated gloves for visualizations of the tape in gloves. See the prior art "Carbon tape Tips", for how to cut, solder, join, coat tape with silicone rubber, etc. See also the prior art document "About carbon fiber tape & carbon fiber rope". In an alternative embodiment, electrically conductive carbon fiber rope can also be used but is not preferred.

There are other resistive materials which can be used, which, when a current is applied thereto, generate heat. This includes the metals copper, silver, alloys, resistive conductive Fabric, See prior art Econ Tex®, and many more.

It is possible to monitor and adjust the breathing chamber temperature with a smart phone, or remote computer, and adjust the current output of the battery with a smart phone or computer. To do so, the face mask includes a controller and a means for communicating between the controller in the face mask and the smart phone, so that the controller can transmit and receive instructions required to control the temperature and/or humidity in the chamber. Preferably, a resistive element is included in the electrical pathway between the battery and the resistive carbon fiber tape to control the amount of electrical energy used to drive or otherwise heat the tape 7. The resistor is adjustable, and limits the current thereby. Such remote control enables a user to conveniently raise or lower the temperature and/or humidity of the air in the breathing chamber. The "Warming Store" sells remote control for battery-heated gloves. In the schematic diagram of FIG. 17, a thermometer with a temperature readout 29 can be provided on the inventive face mask 1 and is connected with a Wi-Fi transmitter 66 to the smart phone. Optionally the humidity inside the chamber formed by the inner frame 9 also can be monitored and transmitted to a smart phone.

Figure 2:
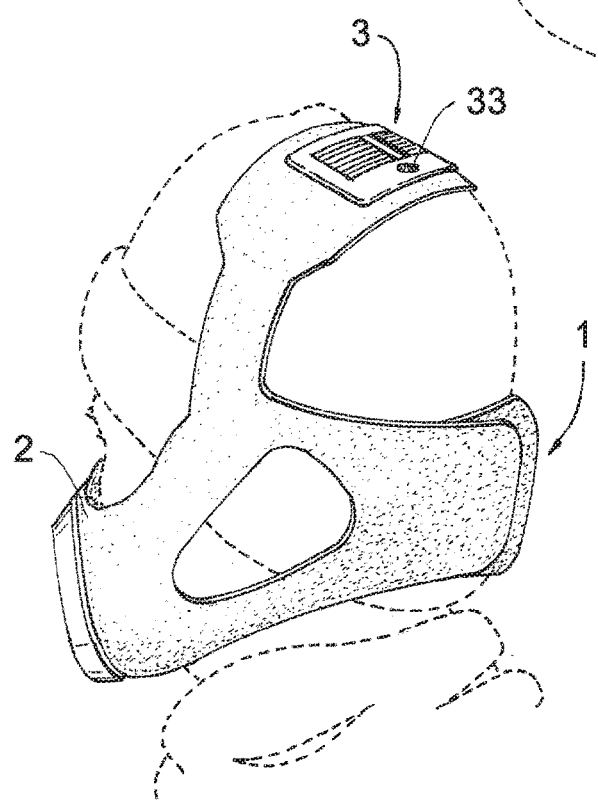
FIG. 2 is a top perspective view of the HE face mask of this invention.

To summarize, the FIGS. 1-19 are reviewed below in greater detail. In FIG. 1, heat exchanger (HE) face mask 1 is shown being worn; in FIG. 2 a top view is shown with a small solar panel 3 installed.

FIG. 3 shows the inner frame 9 with the resistive carbon fiber tape 7 separated for clarity with full inlet plate or valve 5 separated from the front. The face mask 1 includes the resistive carbon fiber tape 7, which is provided in a width of between about 1/64 inch and about 2 and 1/2 inch wide.

FIGS. 4, 5, and 6 show more restrictive inlet plates or valves 11, 13 and 15 respectively which may be used for athletic training.

Figure 9:
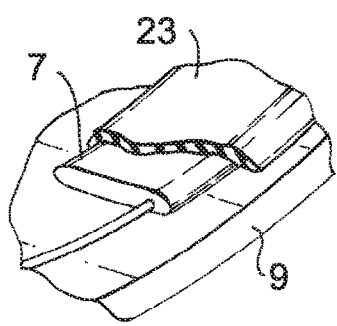
FIG. 9 is a detail of the heat tape attachment and silicone coating on the inner chamber wall.

FIG. 8 illustrates an inner frame 9 with different resistive carbon fiber tape 7 shapes within: horseshoe, crescent or curved u-shaped. Also weep holes 21 are illustrated in FIGS. 8 and 11. FIG. 7 is a detail showing the wiring pigtail at the end of conductive carbon fiber 7 and the return weave 17 conductor terminating in plug 19. FIG. 9 is a detail showing a coated tape 23 which is adhered, and brush coated with silicone to the inner heat chamber wall.

Figure 12:
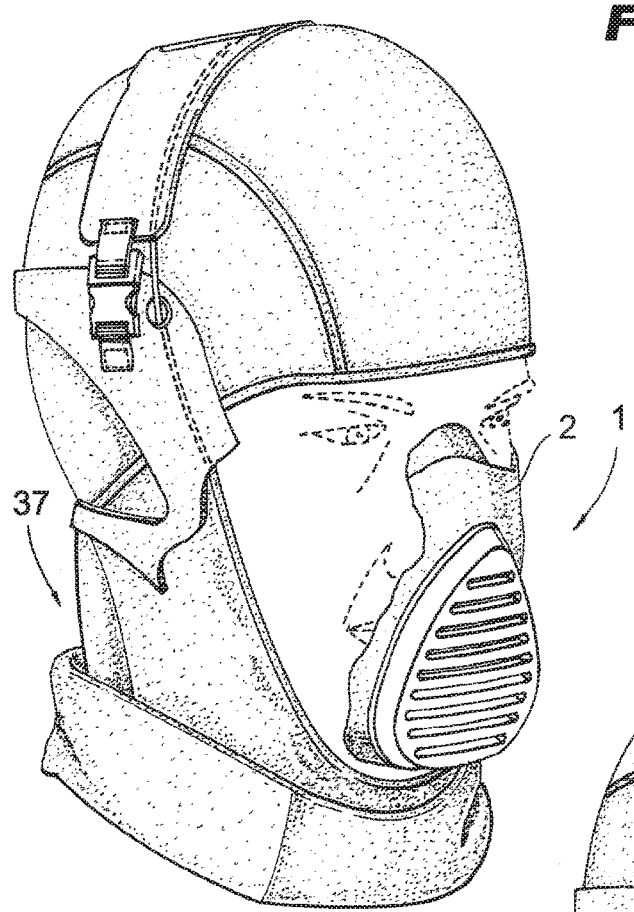
FIG. 12 is a front perspective view in partial cutaway of a user wearing a HE face mask with an open front, with part of the user's hidden face shown exposed.

FIG. 12 is an exploded view of heat and moisture exchange (HME) face mask 1 illustrating some features not previously shown in FIG. 3. Small on-mask battery 25 is visible near zipper compartment 31 where it would normally reside. On/off switch 23 and temperature readout 29 are also shown with temperature adjustment set point potentiometer 35. A larger battery 27 which can be carried in a breast pocket is also shown. Medicine access port 43 is shown on the side of the housing.

FIG. 11 is a cross section of the inner frame 9 showing the intake air flow through inner volume 4 between face plate 5 and the nose and mouth of the user.

Figure 13:
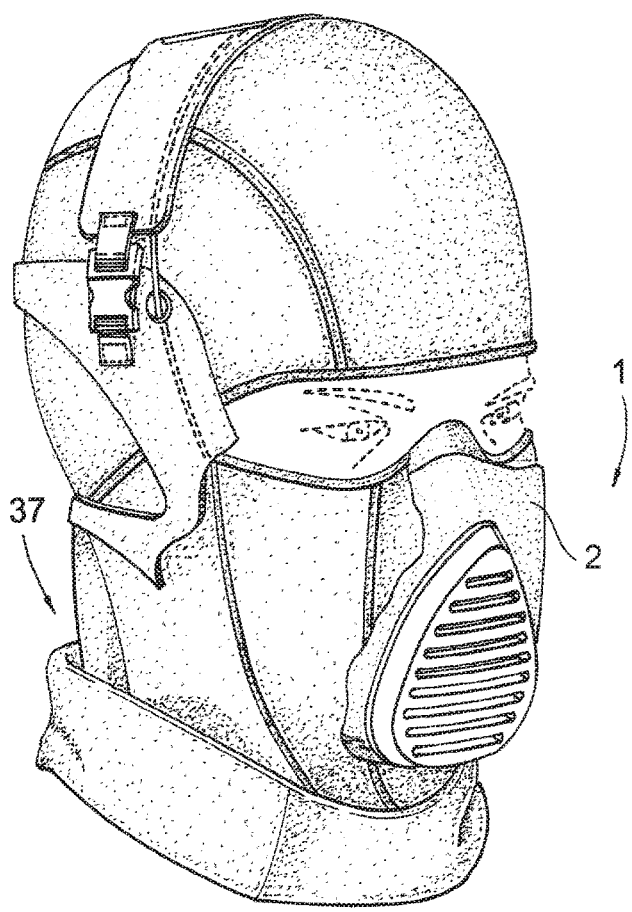
FIG. 13 is a front perspective view of a user wearing a HE face mask with a closed balaclava head covering, showing only the eyes exposed to the environment.
Figure 14:
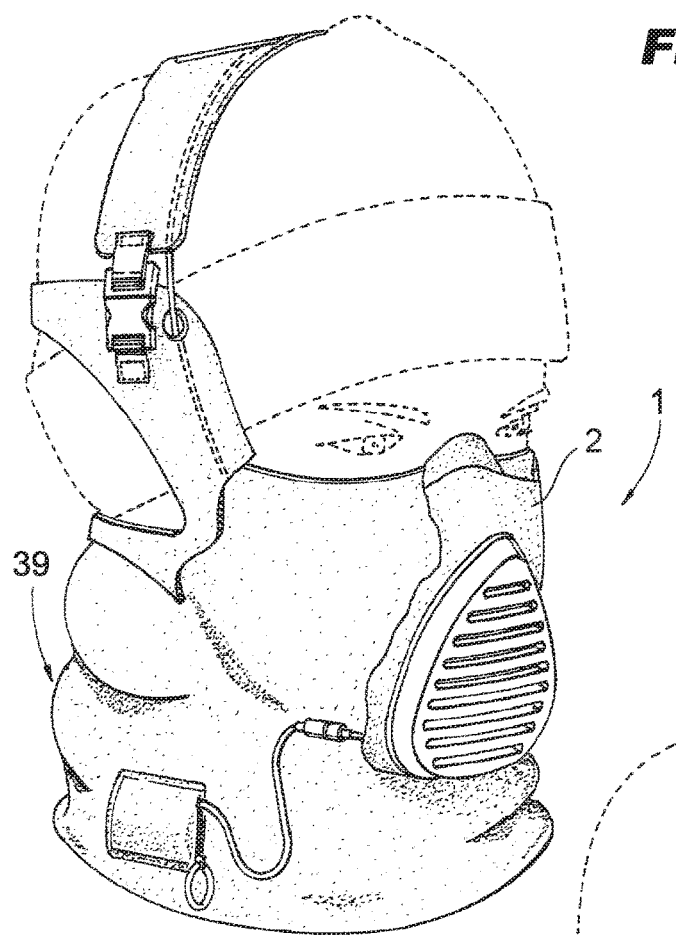
FIG. 14 is a front perspective view of a HE face mask worn over a neck gator.
Figure 15:
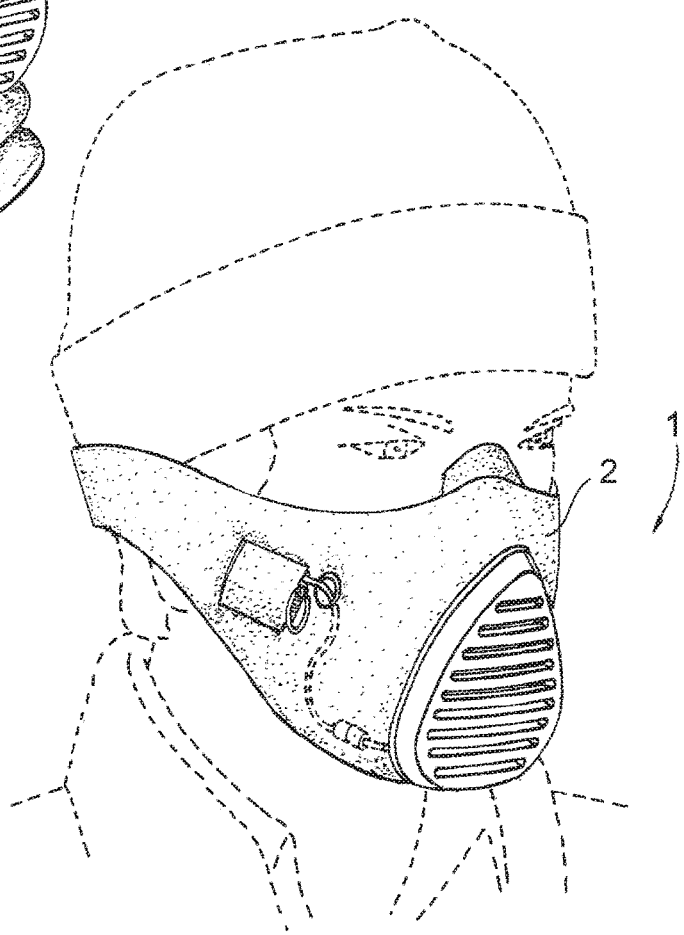
FIG. 15 is a front perspective view of an alternate embodiment showing a stand alone mask including a nasal/mouth covering only, held on the head of the user by one or more skull encircling straps.

FIG. 12 shows a user using mask 1 as part of a balaclava headgear 37, with a partial open front exposing the eyes. Part of the mask 1 with face covering 2 is shown in cutaway. FIG. 13 shows a user with the balaclava headgear 37 of FIG. 12, with the balaclava headgear closed around mask 1. FIG. 14 shows mask 1 being used over neck gator scarf 39. FIG. 15 shows an alternate embodiment of a stand alone mask 1 including a nasal/mouth covering 2 only, held on the head of the user by one or more skull encircling straps. This simplified embodiment enables the user to wear conventional head gear and street clothes, without the excessive covering of a balaclava headgear only exposing the user's eyes.

Figure 16:
FIG. 16 is a perspective view of a man in a wheelchair using a HE face mask in an indoor venue.

FIG. 16 shows a person with a compromised respiratory system, such as COPD, for example, in wheelchair 41 using mask 1 in an indoor area.

Figure 17:
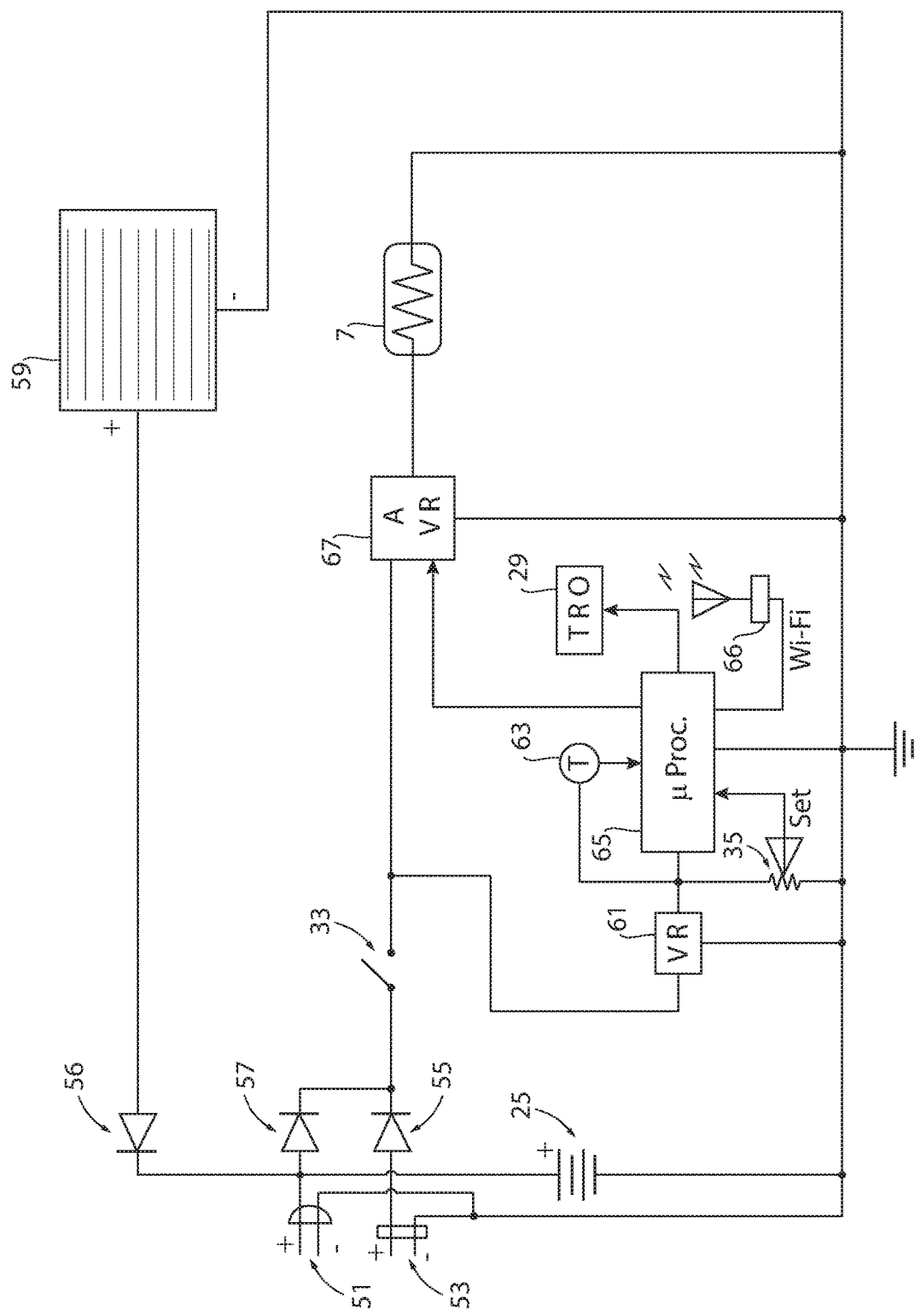
FIG. 17 is a schematic block diagram of a circuit to support the operational aspects of the face mask of this invention.

FIG. 17 is an electrical diagram showing one possible implementation of heat exchanger (HE) face mask 1. Power is derived from small attached battery 25, or a remote battery plugged in at connector 53. Solar panel 59 is wired so as to power the face mask apparatus via steering diodes 56 and 57. Steering diode 55 protects remote battery. Power switch 33 controls operation on/off but does not interrupt charging of battery 25 by either solar panel 39 or a remote charger plugged in at connector 51. Heat tape 7 (if segmented, all segments in series) is driven by adjustable voltage regulator 67 which is regulated by microprocessor 65 which is continuously running a thermostat loop involving digital thermometer 63 with temperature read-out 29. The set point for the temperature setting is either the physical setting of potentiometer 35 or a remote input from a cell phone or computer via Wi-Fi (or Bluetooth) as per user choice. Fixed voltage regulator 61 is used to power microprocessor 65, digital thermometer 63 and set pot 35. If only remote setting of temperature is desired, potentiometer 35 can be eliminated, but the manual option provides redundancy in case of communications problems.

Figure 18:
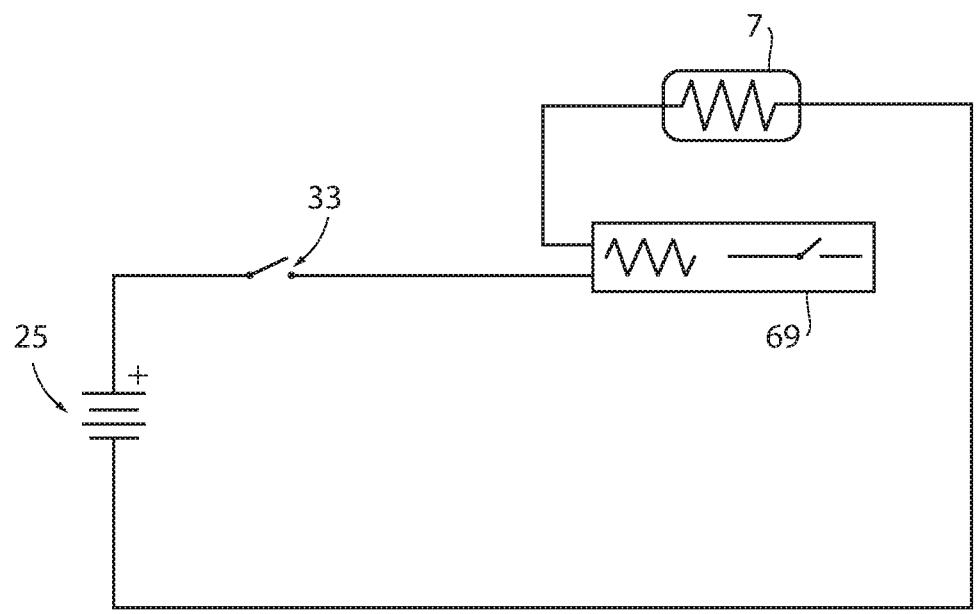
FIG. 18 is a schematic diagram of a simplified HE face mask embodiment with a factory set internal operating temperature.

FIG. 18 shows a schematic diagram of a more simplified embodiment without temperature adjustability. Through testing in the proper cold environment, a factory-installed bimetal thermostat switch 69 of the appropriate rating is selected. This component behaves like a switch which is normally closed below the switching temperature and opens and stays open if the temperature is at or above the switching temperature. In operation it will automatically open and close keeping resistive carbon fiber tape 7 within a narrow range of the switching temperature. This component 69 should be snugged between resistive carbon fiber tape 7 and the wall of inner frame 9 forming the breathing chamber 9. The other two components of the circuit are battery 25 and on/off switch 33.

Figure 19:
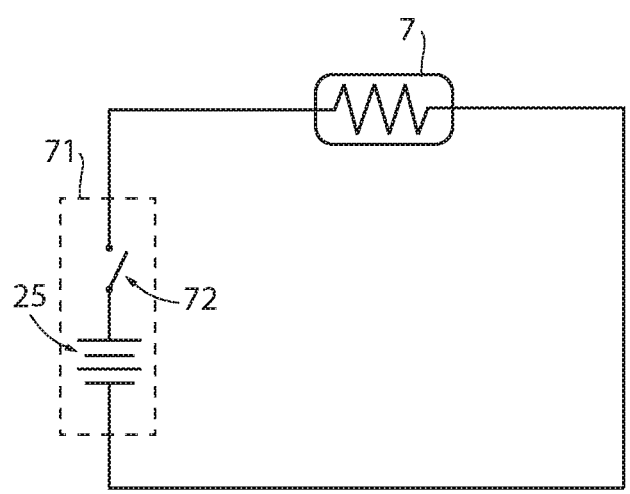
FIG. 19 is a schematic diagram of an even more simplified embodiment of a face mask without a thermostatic element.

FIG. 19 is a further simplification with no thermostatic element resistive carbon fiber tape 7 is directly connected to a battery holder 71 which removably holds battery 25 and provides on/off switch 72 which is part of battery holder 71. The temperature of resistive carbon fiber tape 7 is wholly regulated by the condition of battery 25.

While any kind of suitable battery may be useful for heating the electrically resistive carbon fiber tape segments 7, a preferred example is a Gerbing Gyde 7V 7000 mAh extended-life rechargeable battery with a remote and charger kit, and action heat 5V and 3.7V rechargeable lithium ion batteries.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

What is claimed is:

1. A face mask for conditioning air to be breathed, comprising:
   a facial covering having an inner surface and an outer surface and configured to be removably positioned over a user's mouth and nose, thereby forming an unrestricted breathing chamber with an unimpeded inner volume in which air to be breathed is conditioned;
   wherein said unrestricted breathing chamber includes an opening through which the air to be breathed is drawn and air to be exhaled is expelled;
   an inner frame with an inner and outer surface, wherein the outer surface of the inner frame is attached to the inner surface of the facial covering about the opening; and
   conditioning means having flexible conductive resistive material arranged in said unrestricted breathing chamber on the inner surface of the inner frame located away from said opening in said unrestricted breathing chamber where the air to be breathed is drawn and air to be exhaled is expelled, to condition air drawn into said unrestricted breathing chamber;
   whereby inspired unrestricted and unimpeded cold air is heated in said unrestricted breathing chamber and goes directly in the mouth and nose of the user;

whereby placement and location of said flexible conductive resistive material is within said unrestricted breathing chamber and is completely out of the way of the inspired cold airflow.

2. The face mask of claim 1, wherein the flexible conductive resistive material comprises an electric heating element of resistive carbon fiber tape.

3. The face mask of claim 1, wherein air to be breathed and/or to be exhaled traverses a path through the unimpeded inner volume between a user's mouth and/or nose, and the opening in said unrestricted breathing chamber, surrounded by the inner surface of the inner frame.

4. The face mask of claim 1, wherein the opening in said unrestricted breathing chamber is formed to receive a detachable inlet plate or valve.

5. The face mask of claim 4, wherein the air to be breathed is drawn through the inlet plate or valve and air to be exhaled is expelled through the inlet plate or valve.

6. The face mask of claim 2, wherein the resistive carbon fiber tape is between about 1/64 inch and about 2 and 1/2 inch wide.

7. The face mask of claim 6, wherein the width of the resistive carbon fiber tape is 7/8 inch.

8. The face or mask of claim 4, wherein the inlet plate or valve is detachably connected to the inner frame that is fixed to the inner surface of the facial covering.

9. The face or mask of claim 8, wherein the inlet plate or valve is detachably connected to the inner surface of said unrestricted breathing chamber using a snap or bayonet mount.

10. The face or mask of claim 4, wherein the inlet plate or valve is formed with one or more openings, in the form of slit patterns, and wherein each of the slit patterns is configured to define different resistance to breathing air through the inlet plate or valve.

11. The face mask of claim 10, wherein the different resistances associated with the slit patterns support air resistance training by athletes using the face mask.

12. The face mask of claim 1, wherein said unrestricted breathing chamber is formed with at least one weep hole through which moisture generated as condensation when cold air mixes with moist, warm exhalation air can drain.

13. The face mask of claim 12, wherein the at least one weep hole is arranged in a bottom of said unrestricted breathing chamber.

14. The face mask of claim 12, wherein the inner frame includes at least one weep hole that is aligned with the at least one weep hole within said unrestricted breathing chamber.

15. The face mask of claim 1, wherein the facial covering is manufactured from a material selected from the group of materials consisting of paper, cloth, medical grade polyurethane, medical grade neoprene and medical grade silicone.

16. The face mask of claim 1, wherein the inner frame is manufactured from a material selected from the group of materials consisting of medical grade polyurethane, medical grade neoprene, medical grade silicone and medical grade metals or plastics materials.

17. The face mask of claim 2, wherein the conditioning means includes a source of electrical power for the electric heating element.

18. The face mask of claim 17, wherein the source of electrical power is a battery electrically connected to the conditioning means.

19. The face mask of claim 18, wherein the battery is either rechargeable or disposable.

20. The face mask of claim 17, further comprising a solar-based charging system for supplying electrical power to the face mask, including recharging the battery, or supplying current to the resistive carbon fiber tape.

21. The face mask of claim 17, further comprising a filter unit that filters air to be conditioned prior to breathing.

22. A method of conditioning air to be breathed in reliance upon a face mask that comprises a facial covering having an inner surface and an outer surface and configured to be removably positioned over a user's mouth and nose, comprising the steps of forming an unrestricted breathing chamber with an unimpeded inner volume in which air to be breathed is conditioned, said unrestricted breathing chamber including an opening through which the air to be breathed is drawn and air to be exhaled is expelled, providing an inner frame with an inner and outer surface that defines a contour of said unrestricted breathing chamber, attached attaching flexible conductive resistive material of a conditioning means to the inner surface of the facial covering within said unimpeded inner volume about the opening in said unrestricted breathing chamber, locating said conditioning means having flexible conductive resistive material on the inner surface of the inner frame, to condition air drawn into said unrestricted breathing chamber, the method further comprising the steps of:
attaching the facial covering to a user's face so that it covers the user's mouth and nose to form said unrestricted breathing chamber and said unimpeded inner volume;
activating the conditioning means;
breathing air from outside the face mask into said unrestricted breathing chamber, to mix the outside air with exhaust air from the user, in said unimpeded inner volume, realizing a mixture of air that is drawn into the user's air passages, which is warmer and moister than the outside air;
whereby said air flow is unrestricted and unimpeded and said flexible conductive resistive material of said conditioning means is located away from said opening in said unrestricted breathing chamber where the air to be breathed is drawn and air to be exhaled is expelled,
whereby placement and location of the flexible conductive resistive material conditioning means is within said unrestricted chamber having said unimpeded inner volume and is completely out of the way of the inspired cold airflow.

23. The method of claim 22, wherein the flexible conductive resistive material is resistive carbon fiber tape and the face mask includes an on/off button, and wherein upon activating the on/off button to an on state, a predetermined current is provided to the resistive carbon fiber tape in said unrestricted breathing chamber having said unimpeded inner volume.

24. The method of claim 23, wherein the face mask includes a temperature sensor.

25. The method of claim 24, wherein the temperature sensor is positioned in said unrestricted breathing chamber.

26. The method of claim 22, wherein the flexible conductive resistive material is attached to the inner surface of the inner frame in a pattern selected from a group of patterns consisting of horseshoe, u-shaped or other curvilinear geometric shape.

27. The method of claim 26, wherein said flexible conductive resistive material is resistive carbon fiber tape which is affixed to the inner surface of the inner frame using a fastening material selected from the group consisting of silicone rubber, rubber cement, epoxy and adhesive agents.

28. The method of claim 23, wherein the predetermined current is defined by a battery in series with the resistive carbon fiber tape.

29. The method of claim 28, where the battery is a lithium ion 7.4V battery, a lithium ion 3.7 V battery, a lithium ion 5V battery, or any battery with sufficient current to warm the resistive carbon fiber material.

30. The method of claim 29, where the amount of current supplied is user adjustable based on an adjustable resistance device in line with the resistive carbon fiber tape.

31. The method of claim 29 wherein the predetermined current is automatically determined based on outside temperature.

32. The method of claim 23 wherein the amount of current supplied is adjustable manually.

33. The method of claim 23 wherein the amount of current supplied is adjustable remotely by a specially programmed wireless fob device.

\* \* \* \* \*